United States Patent [19]

Brophy et al.

[11] Patent Number: 5,789,179
[45] Date of Patent: Aug. 4, 1998

[54] CAT ASSAY

[75] Inventors: Gerard Philip Brophy, Cardiff; William Jonathan Cummins, Tring; Christopher Robert Mundy, Cambridge, all of United Kingdom

[73] Assignee: Amersham International plc, United Kingdom

[21] Appl. No.: 861,536

[22] Filed: May 22, 1997

Related U.S. Application Data

[63] Continuation of Ser. No. 334,228, Nov. 4, 1994, abandoned.

[30] Foreign Application Priority Data

Nov. 5, 1993 [EP] European Pat. Off. ............ 93308860

[51] Int. Cl.$^6$ .................... G01N 33/573; G01N 33/53
[52] U.S. Cl. ................... 435/7.4; 435/7.5; 435/7.7; 435/15; 435/964; 436/518; 436/523; 436/524; 436/525; 436/526; 436/527; 436/528; 436/529; 436/530; 436/531; 436/532; 436/533; 436/534; 436/536; 436/542; 436/804
[58] Field of Search ................... 435/7.4, 7.5, 7.7, 435/15, 964; 436/518, 523–534, 536, 542, 804

[56] References Cited

U.S. PATENT DOCUMENTS 4,489,156  12/1984  Khanna et al. .
4,489,157  12/1984  Khanna et al. .
4,568,649   2/1986  Bertoglio-Matte ............ 436/534
5,262,545  11/1993  Haughland et al. ............ 548/405

FOREIGN PATENT DOCUMENTS

0387875A3  9/1990  European Pat. Off. .
2312780    1/1977  France .
WO8903042  4/1989  WIPO .

OTHER PUBLICATIONS

Derwent Abstracts, Database WPI, Week 9127, Derwent Publications Ltd., London, GB; AN91-198111 (1991).

Chemical Abstracts, 90:106x (1979).

Sigma Catalog p. 1122, 1993.

*Primary Examiner*—Sheela Huff
*Attorney, Agent, or Firm*—Wenderoth, Lind & Ponack, L.L.P.

[57] ABSTRACT

A method of assaying for CAT in a fluid involves the use of a complex of chloramphenicol with a member of a specific binding pair such as a hapten or biotin. Biotinylated chloramphenicol is claimed as new. A scintillation proximity assay involves use of this reagent with tritiated acetyl coenzyme A and streptavidin coated SPA beads.

5 Claims, 3 Drawing Sheets

Synthesis of ( + ) - D-threo-6-biotinylamino-N [(2-hydroxy-1-hydroxymethyl)
-2-(4-nitrophenyl) ethyl ]-hexanamide    COMPOUND 1.

Synthesis of 6-biotinylamino-N [ 4-(N-acetyl-1-(2-amino-1,3-propandiol)) phenyl ] hexamide    COMPOUND 2.

CAT ASSAY

This application is a continuation of application, Ser. No. 08/334,228, filed Nov. 4, 1994, now abandoned.

BACKGROUND OF THE INVENTION

Chloramphenicol Acetyl Transferase (CAT) is the most commonly used reporter gene in molecular biology. The enzyme catalyses the reaction of chloramphenicol and acetyl coenzyme A to produce acetylated chloramphenicol. The enzyme has no eukaryotic counterpart and therefore is a useful measure of transfection efficiency and translational activity in cultured cells. Typically the gene, contained on a plasmid, is transfected into the cell of interest and, after an appropriate incubation period, CAT activity is measured.

CAT has a number of advantages for use as a reporter gene:

The enzyme activity is readily distinguishable from that of endogenous cellular proteins present in the cell prior to transfection.

There is no interference or competition from other enzymatic activities in the cells.

CAT is a relatively stable enzyme exhibiting a degree of thermotolerance and a lack of inhibition by cellular components.

PRESENT METHODS OF CAT ACTIVITY DETERMINATION $^{14}$C Chloramphenicol TLC

This is the most common method of assaying for CAT activity. The cell extract containing CAT is incubated with $^{14}$C chloramphenicol and cold acetyl coA. After incubation the reactants are extracted into an organic solvent and dried down. The reactants are resuspended in a small volume and spotted on Thin Layer Chromatography (TLC) plates which are developed to separate chloramphenicol from its acetylated derivatives. The plates are then exposed to autoradiographic film to locate the radioactive spots. These can then be scraped off, extracted and scintillation counted to give a measure of acetylation activity. Alternatively if a radioactive imaging system, such as a phosphorimager, is available the plates can be exposed and directly quantificated by this means.

The disadvantages of this method are as follows:

The assay is cumbersome and time consuming.

The assay involves TLC.

Organic solvents are used.

Quantification is difficult.

Sensitivity is limited.

It is difficult to assay large numbers of samples.

Labelled acetyl coA

A variation on the above assay uses a radioactive acetyl group on the coA and cold chloramphenicol. After the reaction the mix is extracted with organic solvent or overlayed with water immiscible scintillation fluid. Acetylated forms of chloramphenicol diffuse into the organic phase and can be counted.

Disadvantages

The assay is difficult to perform and often yields unsatisfactory results due to phase flipping problems.

Fluorescent chloramphenicol

A chloramphenicol with a fluorescent molecule attached is commercially available. This assay format is carried out by adding this fluorescent chloramphenicol and acetyl coA to the cell extract. The chloramphenicol and its reaction products are separated by TLC and visualised by UV illumination. The spots can be scraped off and quantificated in a fluorimeter.

Disadvantages

The assay is cumbersome and time consuming.

The assay requires a TLC separation step.

Sensitivity is low.

A fluorimeter may not be easily accessible in every laboratory.

CAT ELISA

A CAT ELISA kit is commercially available. In this assay format cell extract is pipetted into MTP wells which contain bound CAT antibody. The wells are washed and incubated with anti-CAT digoxygenin. Again the wells are washed and incubated with anti-digoxygenin peroxidase. The wells are washed and incubated with a peroxidase substrate yielding a colourimetric endpoint which can be quantificated on an MTP reader.

Disadvantages

CAT presence not activity is measured.

The assay is relatively time consuming due to the many washing steps.

Sensitivity is low.

SUMMARY OF THE INVENTION

This invention provides an improved method of assaying for CAT, based on the use of chloramphenicol analogues, some of which are also claimed herein as new compounds.

In one aspect the invention provides a method of assaying for CAT in a fluid, which method comprises incubating in the presence of a sample of the fluid, a chloramphenicol analogue which comprises a member of a specific binding pair, a radiolabelled acyl coenzyme A analogue, and a third reagent which comprises the other member of the specific binding pair, whereby there is formed a complex (third reagent)—(chloramphenicol analogue)—(acyl group) to an extent related to the CAT activity of the fluid sample.

A chloramphenicol analogue is a compound, related to chloramphenicol, which is capable of reacting with acetyl coenzyme A, in a reaction catalysed by CAT, to give the 3-acetyl derivative. The analogue is a modified chloramphenicol derivative, which may for example have lost its dichloroacetyl function. An analogue may be chemically identical to the originating compound; for example, a radiolabelled compound is regarded herein as being an analogue of the unlabelled compound.

Specific binding pairs are well known in biochemistry. They include, but are not limited to: antigen/antibody; hapten/antibody; biotin/avidin; biotin/streptavidin; single stranded DNA/complementary DNA.

The chloramphenicol analogue comprises a member of a specific binding pair, and may be a conjugate of chloramphenicol with the member of the specific binding pair, the conjugate having the structure shown

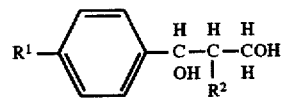

where $R^1$ is —$NO_2$ or —X-Z, $R^2$ is —NHCOR$^3$ or —X-Z, provided that at least one of $R^1$ and $R^2$ is —X-Z.

$R^3$ is $CHCl_2$ or $C_1$–$C_6$ alkyl,

Z is a member of a specific binding pair, e.g. a hapten, and

X is a spacer arm of sufficient length to enable the hapten or other member of a specific binding pair to bind correctly with its specific binding partner.

When $R^1$ is $NO_2$ and $R^2$ is $NHCOCHCl_2$, the compound is chloramphenicol. The two asymmetric carbon atoms generate four possible stereoisomers, of which only the D-threo isomer has significant biological activity. Preferred chloramphenicol analogues are based on this stereoisomer.

Z may be a hapten such as biotin, fluorescein or digoxygenin. The spacer arm X may typically be from 2 to 25 carbon atoms, preferably 6 carbon atoms in length. Certain of these chloramphenicol analogues are new compounds, and are included as such in this invention. Among these are compounds having the formula 1 above in which either $R^1$ is $NO_2$ and $R^2$ is X-biotin, or $R^1$ is X-biotin and $R^2$ is $NHCOCH_3$, and X is a spacer arm of sufficient length to enable the biotin moiety to bind correctly with its specific binding partner. Preferably X contains 6 carbon atoms, so that the compound is either (+)-D-threo-6-biotinylamino-N[(2-hydroxy-1-hydroxymethyl)-2-(4-nitrophenyl) ethyl]-hexamide; or 6-biotinylamino-N[4-(N-acetyl-1-(2-amino-1, 3-propandiol))phenyl] hexamide.

An acyl coenzyme A analogue is a compound, related to acetyl coenzyme A, which is capable of undergoing a reaction with chloramphenicol, catalysed by CAT, resulting in the production of a 3-acyl derivative of chloramphenicol. The acyl coenzyme A analogue may be acetyl coenzyme A, radiolabelled with e.g. tritium or carbon-14. Or the acyl coenzyme A analogue may be an acyl coenzyme A, in which the acyl is e.g. propionyl or butyryl. The acyl group of the acyl coenzyme A analogue is radiolabelled. The nature of the radiolabel is not material to the invention.

The method of the invention involves the use of a third reagent which is or comprises a member of a specific binding pair; the other member of this specific binding pair is comprised in the chloramphenicol analogue. For example, when the biotinylated chloramphenicol analogue is used, the third reagent may be avidin or streptavidin.

The chloramphenicol analogue, the acyl coenzyme A analogue and the third reagent are incubated, in the presence of a sample of the fluid under test, in order to form a complex (third reagent)—(chloramphenicol analogue)—(acyl group).

In this complex, the acyl group is radiolabelled. In order to facilitate separation of the complex from unreacted label, the third reagent may be bound to a solid support, for example to a wall of an assay vessel or to solid particles suspended in the assay medium. The assay reagents may be incubated all together, or alternatively the chloramphenicol analogue may be pre-reacted with the third reagent.

There follow examples of preferred assay formats according to the invention. These involve the use of chloramphenicol-hapten conjugates as the chloramphenicol analogue. The hapten is used for separation/attachment purposes and the radiolabelled acyl group provides the means of detection.

A. SPA-CAT Assay

SPA, the Scintillation Proximity Assay is covered by U.S. Pat. No. 4,568,649, European Patent No. 0154734 and Japanese Patent Application No. 84/52452.

In this assay format a haptenated chloramphenicol analogue (the hapten is preferably biotin) is incubated with tritiated ($^3H$) acetyl coenzyme A. Suitably coated SPA beads (e.g. streptavidin or specific antibodies) are added and bind to the acetylated, haptenated chloramphenicol analogue produced giving rise to a scintillation signal which is a measure of enzyme activity.

The assay is quick and easy to use. Results are possible in one hour after extract production. No separation steps are required and the entire assay procedure can be carried out in one tube.

In addition the assay is very sensitive (at least fifteen fold more sensitive than $^{14}C$ chloramphenicol TLC assays).

B. CAT assay with coated beads

In this assay format tritiated, acetylated, haptenated chloramphenicol analogue is produced as before in a microcentrifuge tube. Suitably coated beads are added which bind to the haptenated molecule. The beads are centrifuged to form a pellet and the supernatant, which contains the unreacted tritiated acetyl coenzyme A, is removed. The pellet is washed and scintillation fluid added. The scintillation signal produced is a measure of CAT activity.

The assay, although not homogeneous, requires only a single separation step and can be carried out in one tube. It is therefore quicker and easier and more sensitive than existing CAT assays.

BRIEF DESCRIPTION OF THE DRAWINGS

Reference is directed to the accompanying drawings in which.

The following examples illustrate the invention.

DETAILED DESCRIPTION

General Details

Biotinamidocaproic acid N-hydroxysuccinimide ester was obtained from Sigma. D-threo-2-amino-1-(4-nitrophenyl)-1,3-propandiol was obtained from Aldrich or produced by base hydrolysis of chloramphenicol. Triethylamine was predistilled from sodium hydroxide. Anhydrous solvents refer to Aldrich Sure Seal bottled material. Other solvents and reagents are available from several commercial sources.

$^1H$ NMRs were obtained on a Jeol 270 MHz machine using $d_4$ MeOH as solvent.

TLCs were run on Kieselgel 60 $F_{254}$ aluminium backed TLC plates using the solvent system quoted.

EXAMPLE 1

Synthesis of (+)-D-threo-6-biotinylamino-N[2-hydroxy-1-(hydroxymethyl)-2-(4-nitrophenyl)ethyl]-hexamide. (Compound 1)

Figure 1:
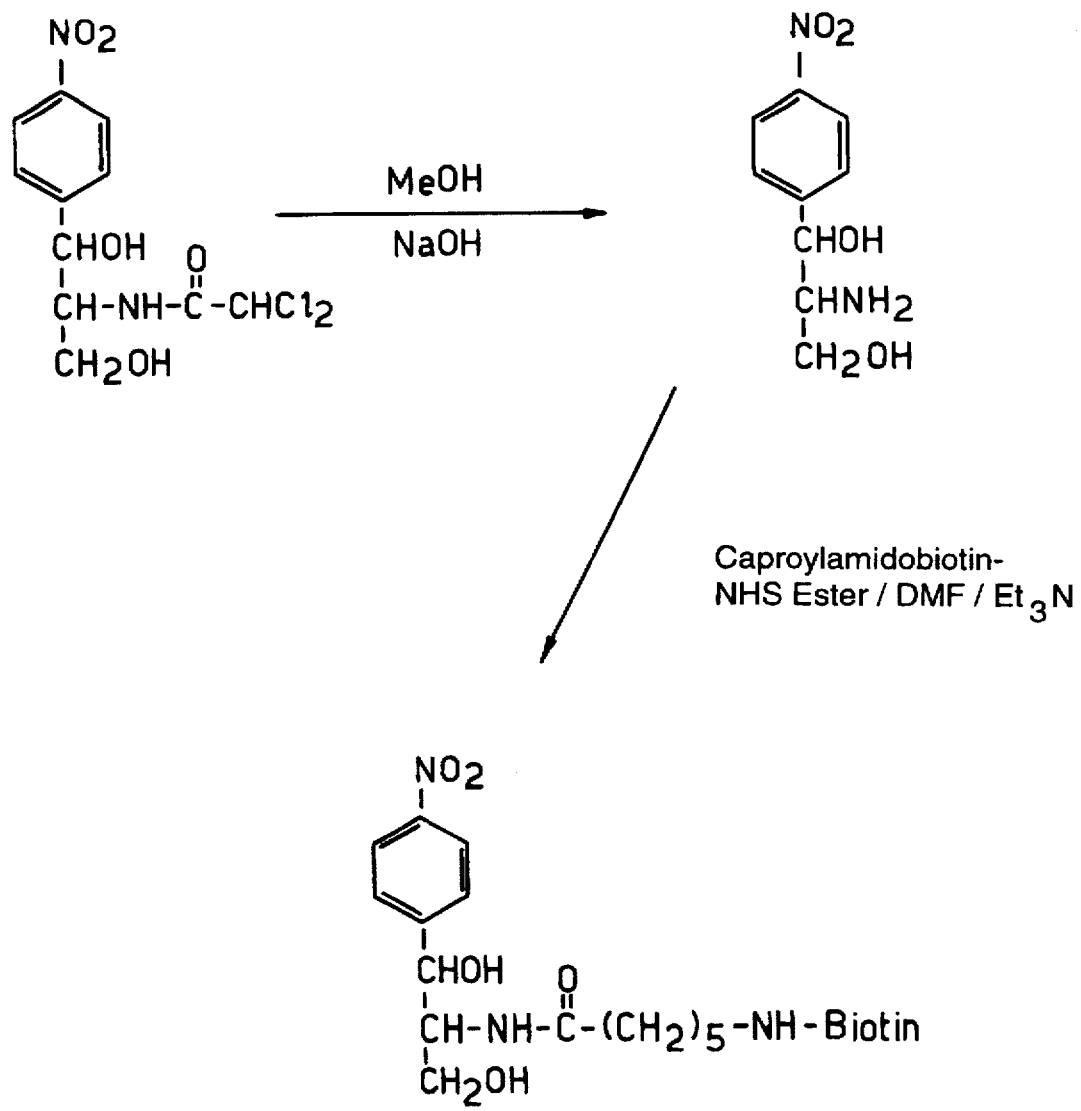
FIG. 1 is a diagram showing the synthesis of (+)-D-threo-6-biotinylamino-N[(2-hydroxy-1-hydroxymethyl)-2-(4-nitrophenyl)ethyl]-hexanamide (Compound 1).

The synthetic reaction sequence is shown in FIG. 1.

In a clean, round-bottom flask biotinamidocaproic acid N-hydroxysuccinimide ester (230 mg 0.51 mmoles) was dissolved in anhydrous dimethylformamide (4 ml). To this was added D-threo-2-amino-1-(4-nitrophenyl)-1,3-propandiol (110 mg 0.52 mmoles) and triethylamine (50 µl). The flask was then stoppered and the contents stirred overnight at room temperature.

Product formation was verified by pipetting 0.5 µl of the reaction onto a TLC plate and developing in chloroform/methanol 9:1. The product has an $R_f$ of 0.2.

The product was purified using a preparative scale reverse phase HPLC column (Hamilton PRP-1 preparative column 21:4 mm id×250 mm). An acetonitrile/water gradient elution was used at a flow rate of 8 ml/min.
Gradient profile

| Time (min) | % acetonitrile |
| --- | --- |
| 0 | 10 |
| 40 | 50 |
| 45 | 100 |
| 50 | 10 |

The product peak's retention time was approximately 30 mins as measured by UV absorption at 254 nm. The solvent from the product fraction was rotary evaporated off and the product was resuspended in ethyl acetate (5 ml). The white solid was filtered on a sintered glass funnel and then air dried. The solid was placed under high vacuum for one hour to remove the last traces of solvent. Yield 200 mg (71%). The melting point was determined as 173° C.–175° C. 270 MHz $^1$H NMR d$_4$MeOH δ: 1.1–1.8 (m, 12H), 2.1 (t, 2H), 2.7 (d, 1H), 2.9 (m, 1H), 3.1 (m, 2H), 3.2 (m, 1H), 3.5 (m, 1H), 3.7 (m, 1H), 4.1 (m, 1H), 4.3 (m, 1H), 4.5 (m, 1H), 5.1 (d, 1H), 7.6 (d, 2H), 8.2 (d, 2H).

Figure 2:
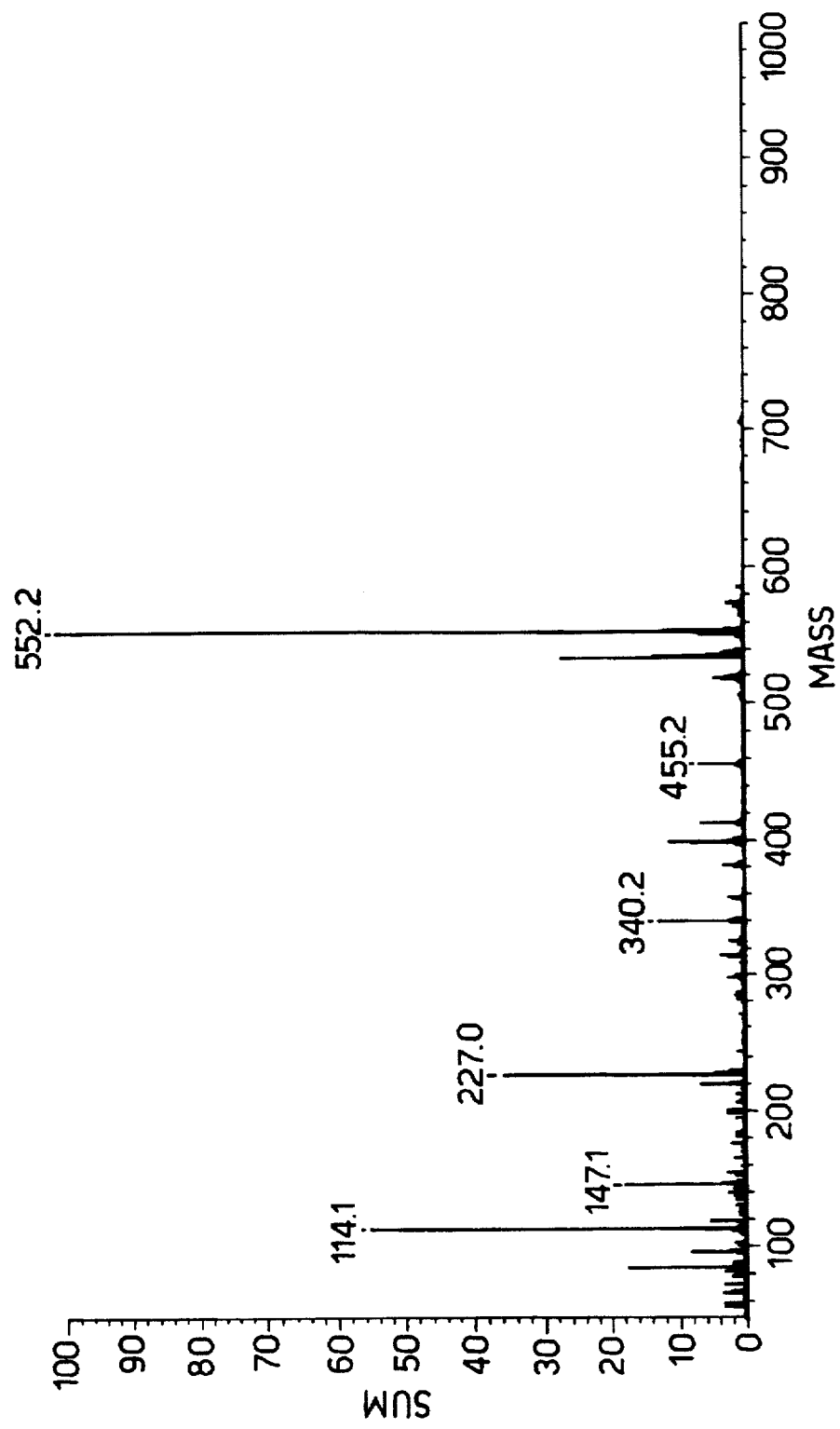
FIG. 2 is a mass spectrometry trace of Compound 1.

The product was analysed by mass spectrometry. A trace is provided in FIG. 2.

A kinetic analysis of CAT and this biotinylated chloramphenicol analogue was carried out to characterise this new substrate. This work determined that the enzyme's Km for chloramphenicol was 11.0 μM and for the biotinylated chloramphenicol analogue was 9.5 μM. The kcats were 97 s$^{-1}$ and 93 s$^{-1}$ respectively. These data indicate that the biotinylated chloramphenicol analogue is a suitable substrate for CAT and that the reaction rates of the enzyme are similar with both substrates.

EXAMPLE 2

Standard curve of Chloramphenicol Acetyl Transferase (CAT) activity.

In this assay the biotinylated chloramphenicol analogue of Example 1 is acetylated by CAT using [$^3$H] acetyl coenzyme A as the acyl donor. The tritiated acetylated biotinylated chloramphenicol analogue binds to Scintillation Proximity Assay (SPA) beads and gives rise to a scintillation signal which can be related to enzyme activity.

Materials and Methods

CAT enzyme obtained from Professor W. V. Shaw, Biochemistry Department, Leicester University, was diluted to concentrations of 0.02, 0.04, 0.06, 0.08 and 0.1 units of enzyme with 0.1M Tris/HCl (pH 7.8) in total volume of 40 μl. One unit of enzyme is the amount which catalyses the acetylation of one nanomole of chloramphenicol in one minute at 37° C. Duplicate samples were assayed. To each assay tube was added 10 μl of a master mix which contained:

| | |
| --- | --- |
| biotinylated chloramphenicol analogue (0.1 mmolar) | 1 μl |
| [$^3$H] acetyl coenzyme A (Amersham TRK688) | 2 μl (0.5 μCi) |
| water | 1 μl |
| Tris/HCl, pH 7.8, 1 molar | 6 μl. |

The reaction mixture was mixed and incubated at 37° C. for 30 minutes.

After incubation 0.5 mg of streptavidin coated SPA beads (Amersham) were added in 0.75 ml PBS. The reaction tubes were placed in scintillation vials and counted.

The results are tabulated below.

| CAT (units) | cpm |
| --- | --- |
| 0 | 181 |
|   | 197 |
| 0.02 | 11304 |
|   | 11485 |
| 0.04 | 24026 |
|   | 23873 |
| 0.06 | 34921 |
|   | 34957 |
| 0.08 | 46748 |
|   | 45050 |
| 0.1 | 50846 |
|   | 52762 |

As can be seen the increase in CAT activity is proportional to the increase in cpm.

EXAMPLE 3

Synthesis of 6-biotinylamino-N[4-(N-acetyl-1-(2-amino-1, 3-propandiol))phenyl]hexamide (Compound 2).

Figure 3:
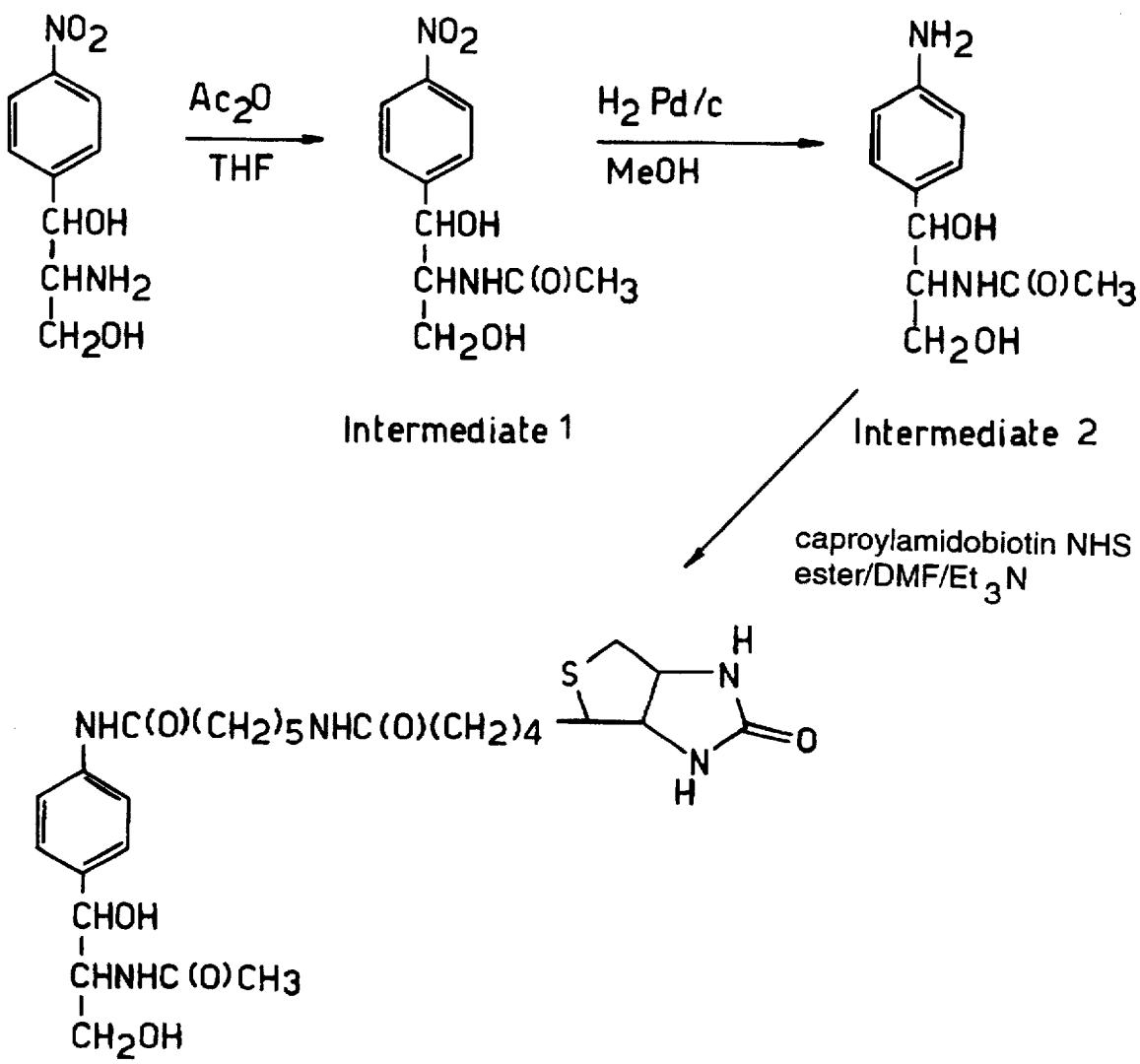
FIG. 3 is a diagram showing the synthesis of 6-biotinylamino-N[4-(N-acetyl-1-(2-amino-1,3-propandiol))phenyl]hexamide (Compound 2).

The synthetic reaction sequence is shown in FIG. 3.

The synthetic details for each intermediate compound in the synthetic sequence and for the final synthetic step are set out below.

N-[2-hydroxy-1-(hydroxymethyl)-2-(4-nitrophenyl)ethyl] acetamide. Intermediate 1

In a clean, round bottom flask D-threo-2-amino-1-(4-nitrophenyl)-1,3-propandiol (1.43 g, 6.75 mmoles) was suspended in anhydrous tetrahydrofuran (30 ml). To this was added acetic anhydride (0.8 ml, 8.44 mmoles). The flask was stoppered and the contents stirred at room temperature for one hour.

Product formation was verified by spotting a small aliquot of the reaction mixture onto a TLC plate and developing in ethyl acetate/methanol 9:1. The product has an R$_f$ of 0.33 and is negative to a ninhydrin spray.

The tetrahydrofuran was removed on a rotary evaporator and the resulting gummy residue subjected to a silica flash column to purify the product. The eluant for the column was ethyl acetate/methanol 9:1. The product fractions were pooled and the solvent removed on a rotary evaporator. The resulting foam was placed under high vacuum for one hour to remove the last trace of solvent. The yield was 1.28 g (78%). 270 MHz $^1$H NMR d$_4$MeOH δ: 1.8 (s, 3H), 3.5 (m, 1H), 3.7 (m, 1H), 4.1 (m, 1H), 5.1 (brs, 1H), 7.6 (d, 2H), 8.2 (d, 2H).

N-[2-hydroxy-1-(hydroxymethyl)-2-(4-aminophenyl)ethyl] acetamide. Intermediate 2

In a clean, round bottom flask N-[2-hydroxy-1-(hydroxymethyl)-2-(4-nitrophenyl)ethyl] acetamide (1.27 g 5 mmoles) was dissolved in methanol (50 ml). The flask was then fitted with a suitable adaptor and coupled to an hydrogenation apparatus. The atmosphere in the flask was then replaced with nitrogen. The adaptor was then removed and 10% palladium on carbon catalyst (466 mg) was added to the flask. The adaptor was replaced and the hydrogenation apparatus manipulated to replace the atmosphere in the flask with hydrogen. The flask contents were then stirred at room temperature under an atmosphere of hydrogen overnight. The hydrogenation apparatus was manipulated to replace the atmosphere in the flask with nitrogen. The flask was then disconnected from the hydrogenation apparatus.

The palladium on carbon catalyst was removed by filtering through a hyflo filter pad. The solvent from the product was rotary evaporated off to give a gum. The gum was placed under high vacuum for one hour to remove the last traces of solvent. The yield of product was 1.05 g (94%). 270 MHz $^1$H NMR d$_4$MeOH δ: 1.9 (s, 3H), 3.4 (m, 1H), 3.6 (m, 1H), 4.0 (m, 1H), 4.7 (d, 1H), 6.7 (d, 2H), 7.1 (d, 2H).

The Intermediate 2 product was used in the next synthetic step without any purification.

6-biotinylamino-N[4-(N acetyl-1-(2 amino-1,3-propandiol))phenyl]hexamide

Biotinamidocaproic acid N-hydroxysuccinimide ester (100 mg 0.22 mmoles) was weighed out into a clean, round bottomed flask. A solution of N-[2-hydroxy-1-(hydroxymethyl)-2-(4-aminophenyl)ethyl] acetamide (108 mg, 0.51 mmoles) in anhydrous dimethylformamide (2 ml) was added to the flask. Triethylamine (25 µl) was added to the flask which was then stoppered. The reaction mixture was stirred at room temperature for a total of 80 hours and at 80° C. for a total of 6 hours.

The major product was then purified using a preparative scale reverse phase HPLC column (Hamilton PRP-1 preparative column 21.4 mm id×250 mm). An acetonitrile/ammonia solution (2ml of 0.880 NH$_3$/litre of water) gradient elution was used at a flow rate of 8 ml/min.

Gradient profile

| Time (min) | % acetonitrile |
|---|---|
| 0 | 0 |
| 45 | 40 |
| 50 | 100 |
| 55 | 0 |

The product peak retention time was approximately 35 min as measured by UV absorption at 254 mm. The solvent from the product fraction was rotary evaporated off to give an off white solid, the yield was 24 mgs (20%). 270 MHz $^1$H NMR d$_4$MeOH δ: 1.2–1.7 (m, 12H), 1.9 (s, 3H), 2.1 (t, 2H), 2.3 (t, 2H), 2.6 (d, 1H), 2.8 (m, 1H), 3.1 (m, 3H), 3.4 (m, 1H), 3.5 (m, 1H), 4.0 (m, 1H), 4.3 (m, 1H), 4.4 (m, 1H), 7.2 (d, 2H), 7.4 (d, 2H).

EXAMPLE 4

6-biotinylamino-N[4-(N-acetyl-1-(2-amino-1,3-propandiol))phenyl]hexamide, (Compound 2) is a substrate of CAT.

Biotinylated chloramphenicol analogue (compound 2) was dissolved to a concentration of 2 mmolar in 50% methanol. $^{14}$C acetyl coenzyme A (50 µCi/ml, 58 mCi/mole) was obtained commercially.

In a microcentrifuge tube were mixed Tris/HCl (1M, pH 7.8) 7.5 µl, biotinylated chloramphenicol analogue (2 mM) 80 µl, CAT enzyme 3.75 units and $^{14}$C acetyl coenzyme A 2 µl (0.1 µCi). The mix was incubated at 37° C. for 90 minutes. A control reaction which contained no enzyme was performed in parallel. 20 µl of each reaction was spotted on to a cellulose TLC plate which was developed in 95/5 chloroform methanol. The TLC plate was exposed to autoradiographic film.

The lane corresponding to the reaction to which enzyme was added contains a spot which migrated under the influence of the solvent. This band is acetylated, biotinylated chloramphenicol analogue. No corresponding band is visible in the no enzyme control.

This experiment proves that 6-biotinylamino-N[4-(N acetyl-1-(2-amino-1,3-propandiol))phenyl]hexamide is acetylated with $^{14}$C acetyl coenzyme A by CAT.

We claim:

1. A method of assaying for CAT in a fluid, which method comprises incubating in the presence of a sample of the fluid; a biotinylated chloramphenicol which comprises a member of a specific binding pair; a radiolabelled acyl coenzyme A; and a third reagent which is the other member of the specific binding pair, and is bound to a solid support, wherein there is formed a complex;

streptavidin or avidin—(chloramphenicol)—(acyl group) to an extent related to the CAT activity of the fluid sample, said complex being bound to the said solid support.

2. The method as claimed in claim 1, wherein the acyl coenzyme A is radioactively labelled acetyl coenzyme A.

3. The method as claimed in claim 1, wherein the acyl coenzyme A is acetyl coenzyme A labelled with tritium, and the third reagent is immobilized on a solid support.

4. The method as claimed in claim 1, wherein the solid support is a scintillation proximity assay support.

5. The method as claimed in claim 1, wherein the chloramphenicol analogue is (+)-D-threo-6-biotinylamino-N[(2-hydroxy-1-hydroxymethyl)-2-(4-nitrophenyl) ethyl]-hexamide.

* * * * *